United States Patent
Albrektsson et al.

(10) Patent No.: US 6,221,076 B1
(45) Date of Patent: Apr. 24, 2001

(54) BONE REAMER FOR SHARPING BONE SOCKETS OR CAVITIES DURING ORTHOPAEDIC SURGERY

(75) Inventors: Björn Albrektsson, Fjärås; Lars Carlsson, Kullavik; Magnus Jacobsson, Göteborg; Tord Röstlund, Kullavik; Stig Wennberg, Gunnilse, all of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/029,683

(22) PCT Filed: Jan. 21, 1998

(86) PCT No.: PCT/SE98/00084

§ 371 Date: Mar. 3, 1998

§ 102(e) Date: Mar. 3, 1998

(87) PCT Pub. No.: WO98/33441

PCT Pub. Date: Aug. 6, 1998

(30) Foreign Application Priority Data

Jan. 31, 1997 (SE) .................................................. 9700300

(51) Int. Cl.[7] ................................................... A61B 17/00
(52) U.S. Cl. ................................. 606/80; 407/54; 407/62
(58) Field of Search .................................. 606/80, 81, 83, 606/84, 85; 623/22.12, 908; 407/42, 54, 61, 62; 408/227

(56) References Cited

U.S. PATENT DOCUMENTS

| 3,412,733 | * | 11/1968 | Rose ........................................ 606/81 |
| 3,702,611 | | 11/1972 | Fishbein . |
| 4,131,116 | | 12/1978 | Hedrick . |
| 4,611,587 | * | 9/1986 | Powlan ................................. 606/81 |
| 4,621,637 | | 11/1986 | Fishbein . |
| 4,662,891 | * | 5/1987 | Noiles ................................... 606/80 |
| 5,007,911 | | 4/1991 | Baker . |
| 5,100,267 | * | 3/1992 | Salyer .................................... 606/81 |
| 5,203,653 | | 4/1993 | Kudla . |
| 5,358,532 | | 10/1994 | Evans et al. . |
| 5,376,092 | * | 12/1994 | Hein et al. ............................ 606/81 |
| 5,405,396 | | 4/1995 | Heldreth et al. . |
| 5,501,686 | * | 3/1996 | Salyer .................................... 606/83 |
| 5,709,688 | * | 1/1998 | Salyer .................................... 606/81 |
| 5,755,719 | * | 5/1998 | Frieze et al. ......................... 606/81 |
| 5,776,263 | | 6/1998 | Grundei et al. . |

FOREIGN PATENT DOCUMENTS

| 3101333 | 12/1981 | (DE) . |
| 3322978 | 1/1985 | (DE) . |
| 0508710 | 10/1992 | (EP) . |
| 0640325 | 3/1995 | (EP) . |
| 0552950 | 9/1996 | (EP) . |
| 1031888 | 6/1953 | (FR) . |
| 1041311 | 10/1953 | (FR) . |
| 9517140 | 6/1995 | (WO) . |
| 9807393 | 2/1998 | (WO) . |

* cited by examiner

Primary Examiner—Gene Mancene
Assistant Examiner—Eduardo C. Robert
(74) Attorney, Agent, or Firm—White & Case LLP

(57) ABSTRACT

The invention is directed to a reamer for shaping a bone socket such as an acetabular cavity. The reamer comprises a cutting head for removing material from the socket during rotation of the cutting head. The cutting head comprises a number of relatively long main cutting edges, each of which extends in a direction from a base to a top of the reamer, and a number, higher than the number of main cutting edges, of relatively short peripheral cutting edges, which are located at the base and distributed at angulary spaced intervals about a rotational axis. The invention also provides a method for implanting a prosthesis component into a bone socket. During shaping of the bone socket, a top portion of the reamer is completely received in the bone socket to such an extent, that a cylindrical entrance portion is formed in the socket. The invention also provides a kit including a reamer and a prosthesis.

19 Claims, 4 Drawing Sheets

BONE REAMER FOR SHARPING BONE SOCKETS OR CAVITIES DURING ORTHOPAEDIC SURGERY

TECHNICAL FIELD OF THE INVENTION

The invention relates to the field of bone cutters or reamers for shaping bone sockets or cavities to a desired form during orthopaedic surgery.

BACKGROUND ART

The invention is especially, but not exclusively, applicable to the field of reaming hip-joint cavities (acetabulea) in the pelvis to a desired form, in preparation for inserting an acetabular cup. Therefore, the technical background to the invention will be described with specific reference to cutters or reamers for shaping acetabular cavities and the problems encountered when using prior-art cutters. A preferred embodiment of the reamer according to the invention is especially useful in connection with the type of acetabular cups disclosed in WO 95/17140. However, the invention may be used also in connection with the shaping of other sockets for receiving artificial joint prosthesis components.

One conventional type of reamer for shaping bone sockets comprises a cutting head, which in use is rotated about a rotational axis for removing material from the socket, and which cutting head is formed by a fully hemispherical wall defining an essentially closed internal chamber. A plurality of relatively small, outwardly projecting, bowl-shaped cutting elements, each defining a small cutting edge, are punched out from or otherwise formed in the hemispherical wall. This design is normally referred to as a "cheese grater". Each cutting element forms a narrow passage leading from the exterior hemispherical surface into the internal chamber of the cutting head. In order to avoid undesired interference phenomena during the reaming operation, the cutting elements are normally distributed in an asymmetrical pattern over the hemispherical surface. Especially, the cutting elements may be distributed along a spiral line as seen in the direction of the rotational axis.

A drawback of this conventional type of reamer having an essentially closed configuration and a plurality of small bowl-shaped cutting elements is that loose cut-off material (debris) will be present at the site of the cutting operation. This is a consequence of the essentially closed configuration of the cutting head and the fact that the bowl-shaped cutting members form only narrow passages for the cut-off material. The presence of loose material at the cutting site may lead to an inaccurate cavity preparation, whereby undesired gaps will be present between the reamed cavity surface and the subsequently inserted acetabular cup. Bone growths cannot bridge too large a gap, so that a portion of the cup surface will be too distant from bone to allow proper attachment. As a result, an optimal cup fixation cannot be obtained, especially in the case of uncemented prosthesis components, where such gaps may reduce initial and long term stability. Also, loose material will clog the reamer, causing an undesired excessive heat generation in the bone tissue, which may damage the bone-tissue viability and thereby reduce its capacity to form new bone. New bone formation is essential for obtaining osseointegration.

Another drawback of this prior-art reamer is that the cutting operation effected by the relatively small, bowl-shaped cutting elements will not result in a smooth cavity surface. Instead, each bowl-shaped cutting element creates circumferentially directed "macro"-grooves in the socket surface during the reaming operation.

A further drawback of this conventional-type reamer is that the asymmetrical distribution of the cutting elements may generate an unintentional "wobbling" of the reamer during rotation thereof. More specifically, as a result of the cutting elements not being symmetrically arranged over the hemispherical surface, the counter-forces generated at each cutting point may together lead to a situation where the cutting head is unequally loaded. The resultant load acting on the cutting head may therefore displace and/or tilt the axis of rotation, whereby the cavity will receive an undesired shape, such as an elliptical cross section.

The above-mentioned drawback related to the formation of circumferentially directed grooves may be reduced by replacing the relatively small bowl-shaped cutting elements with longer cutting edges extending in essentially radial planes along the hemispherical surface, as shown in U.S. Pat. No. 4,131,116. This document discloses a bone cutter for shaping a socket, such as a hip socket, comprising a cutting head located at one end of a rotatably driven shaft and having a fully hemispherical portion with a substantially closed exterior surface. The hemispherical portion defines an essentially closed, hollow internal chamber, and is provided with a number of slots connecting the exterior surface and the internal chamber. A cutting edge, raised slightly above the hemispherical surface, is provided at each slot for moving bone material from the socket into the internal chamber. In the disclosed embodiment, one cutting edge extends past the pole region, i.e. the point where the axis of rotation intersects the hemispherical surface, such that also the bottom of the socket will be reamed.

Resilient quick release means are arranged for connecting and disconnecting the cutting head and the shaft. A cylindrical portion integral with the base of the hemispherical portion is arranged for limiting outward movement of said resilient quick release means.

This prior-art document also describes a conventional reaming technique of starting with a cutting head of smaller radius and increasing the size of the cutting head in increments to enlarge the radius of the socket.

A drawback with the design disclosed in U.S. Pat. No. 4,131,116 is that are undesired "catching" or "biting" effect may occur between the cutting means and the cavity edge, especially each time the cutting head diameter is increased.

Another drawback inherent in cutting heads in the form of a full spherical dome is that it is difficult to guide the reamer precisely along the intended rotational axis without tilting the cutting head in the bone socket.

It is, therefore, an aim of the invention to provide a reamer by which the shaping or preparation of a bone socket can be performed more precisely.

A specific aim of the invention is to provide a reamer by which the above-mentioned "catching effect" is eliminated or at least substantially reduced.

A further aim of the invention is to provide a reamer which eliminates or at least substantially reduces the above-mentioned problem of cut-off material present at the cutting site between the reamer and the bone socket.

A yet further aim of the invention is to provide a reamer by which a smooth inner surface of the socket can be obtained.

Another further aim of the invention is to provide a reamer which is more easy to guide along a predetermined rotational axis during the reaming operation, in order to avoid tilting of the reamer relative to said axis.

It is also an aim of the invention to provide a method for implanting a prosthesis component in a bone socket, by which method the shaping or preparation of the bone socket can be performed more precisely, and to provide a kit for use in performing such a method.

DISCLOSURE OF THE INVENTION

Thus, a reamer according to the invention for shaping a bone socket, such as a acetabular cavity (acetabulum), comprises a cutting head having a top which in use is directed towards the bone socket, and a base axially spaced from the top along a rotational axis of the cutting head. The cutting head is provided with cutting means for removing material from the socket during the rotation of the cutting head about the rotational axis. The reamer according to the invention is characterised in that the cutting means comprises a number of relatively long main cutting edges, each of which extends in a direction from the base to the top, and a number, higher than said number of main cutting edges, of relatively short peripheral cutting edges, which are located at the base of the cutting head and distributed at angulary spaced intervals about said rotational axis.

The reamer according to the invention makes it is possible to perform a more precise shaping or reaming operation of a bone socket, compared with the prior-art reamers or bone cutters. By arranging more cutting edges in the periphery than in the top portion, the load or pressure on the peripheral cutting edges will be reduced compared with the load on the main cutting edges. The reduced load on the peripheral cutting edges will reduce the above-mentioned "catching", while the load on the main cutting edges can be kept at a sufficiently high level to ensure a proper cutting operation. Also the problem related to the presence of cut-off material in the cutting area is reduced. This is due to the fact that the number of the main cutting edges in the top portion can be limited to such an extent that the cut-off material can effectively be removed in the regions between the main cutting edges. The inventive reamer is also advantageous in relation to the first-mentioned cutter having small bowl-shaped cutting edges. In the inventive reamer, each of said main cutting edges will follow the curvature of the bone cavity such that no cutting grooves are created.

In a preferred embodiment, each of the main cutting edges is formed by a respective leg, extending between and interconnecting the top and the base of the cutting head. In the regions between adjacent legs, material-receiving openings are provided for guiding the cut-off material into an interior chamber of the cutting head. The cutting head will thereby present an essentially cage-like, substantially open design. In this context it should be noted that the reamer might work also with one single main cutting edge.

In a preferred embodiment, the number of peripheral cutting edges is at least twice the number of main cutting edges. If the number of peripheral cutting edges is an integer multiple of the number of main cutting edges, it is possible to evenly distribute the peripheral cutting edges relative to the main cutting edges. Within the scope of the invention, these two numbers, and the ratio between them, may vary substantially.

In order to obviate interference phenomena during the reaming operation, the main cutting edges can be "ribbed". This implies that at least some of the main cutting edges are divided by notches or the equivalent into smaller cutting edge portions, and that the notches are arranged in different patterns in adjacent main cutting edges. The purpose of "ribbing" the main cutting edges is to ensure that each main cutting edge always will maintain proper contact with the socket surface during the reaming operation. If the edges are not ribbed there is a risk that the edges might "jump" on the socket surface, leading to undesired interference phenomena.

Another way of reducing interference phenomena is to arrange the main cutting edges and/or the peripheral cutting edges in an asymmetrical pattern about the rotational axis, i.e. with varying angular spacings between the cutting edges.

It is preferred that the cutting head comprises a portion in the form of a truncated dome, the pole region of which defines the top of the cutting head, wherein each of the main cutting edges extends in a direction from a base region of the dome towards the pole region of the dome. This embodiment is advantageous in that a cylindrical entrance portion can be formed in the socket without increasing the depth of the shaped cavity unacceptably. The purpose of providing such a cylindrical entrance portion in the socket will be explained in the following. In an especially preferred variant of this embodiment, the cutting head is further provided with a cylindrical base portion connected to such a truncated dome portion. During the shaping of the bone socket, the dome-shaped portion of the cutting head is completely received in the bone socket to such an extent, that said cylindrical entrance portion is formed in the socket by said cutting means and, thereby, the cylindrical portion of the cutting head is received at least partly in said cylindrical entrance portion of the socket. As a result, the cylindrical portion of the cutting head is effectively guided and centred by the socket during the reaming operation, thereby avoiding, or at least substantially restricting, unintentional tilting of the cutting head.

A method according to the invention for implanting a prosthesis component in a bone socket, such as an acetabular cavity (acetabulum), comprises the step of shaping the bone socket to a desired form for receiving the prosthesis component, and the step of subsequently inserting the prosthesis component into the bone socket. The method is characterised in that the step of shaping the bone socket is performed by the use of a rotational-type reamer having a cutting head, which comprises a top portion provided with cutting means for the removal of material from said bone socket, and a cylindrical base portion, and, in that, during said step of shaping the bone socket, the top portion of the cutting head is completely received in the bone socket to such an extent, that a cylindrical entrance portion is formed in the socket by said cutting means and, thereby, the cylindrical portion of the cutting head is received at least partly in said cylindrical entrance portion of the socket. As a result, the cylindrical portion of the cutting head will be effectively guided and centred by the cylindrical portion of the socket wall, whereby any unintentional tilting of cutting head during the reaming operation can be avoided or at least reduced.

According to another aspect of the invention, there is also provided a reamer for shaping a bone socket, such as an acetabular cavity, comprising a cutting head having a top which in use is directed towards the bone socket, and a base axially spaced from the top along a rotational axis of the cutting head, said cutting head being provided with cutting means for removing material from the socket during rotation of the cutting head about the rotational axis. The reamer is characterised in that said cutting means comprises a number of relatively long main cutting edges, each of which extends in a direction from the base to the top, and in that the base of the cutting head has a cylindrical outer peripheral surface concentric with and parallel to the rotational axis, whereby, in use of the reamer, said cylindrical outer peripheral surface is received at least partly in the socket and guided thereby for preventing or reducing unintentional tilting of the rotational axis.

The above and other features and advantages of the invention are set out in the claims and will be apparent from the following detailed description of an exemplary embodiment of a reamer according to the invention.

BRIEF DESCRIPTION OF THE DRAWINGS

FIG. 1–7 illustrates a reamer according to a preferred embodiment of the invention, wherein:

FIG. 1 is a side elevational view;

FIG. 2 is a top elevational view;

FIG. 3 is a bottom elevational view;

FIG. 4 is a top perspective view;

FIG. 5 is a bottom perspective view;

FIG. 6 is a transverse section taken along the line VI—VI in FIG. 2;

FIG. 7 is an enlarged top elevational view of a portion of the reamer shown in FIG. 2.

DETAILED DESCRIPTION OF A PREFERRED EMBODIMENT

Figure 8:
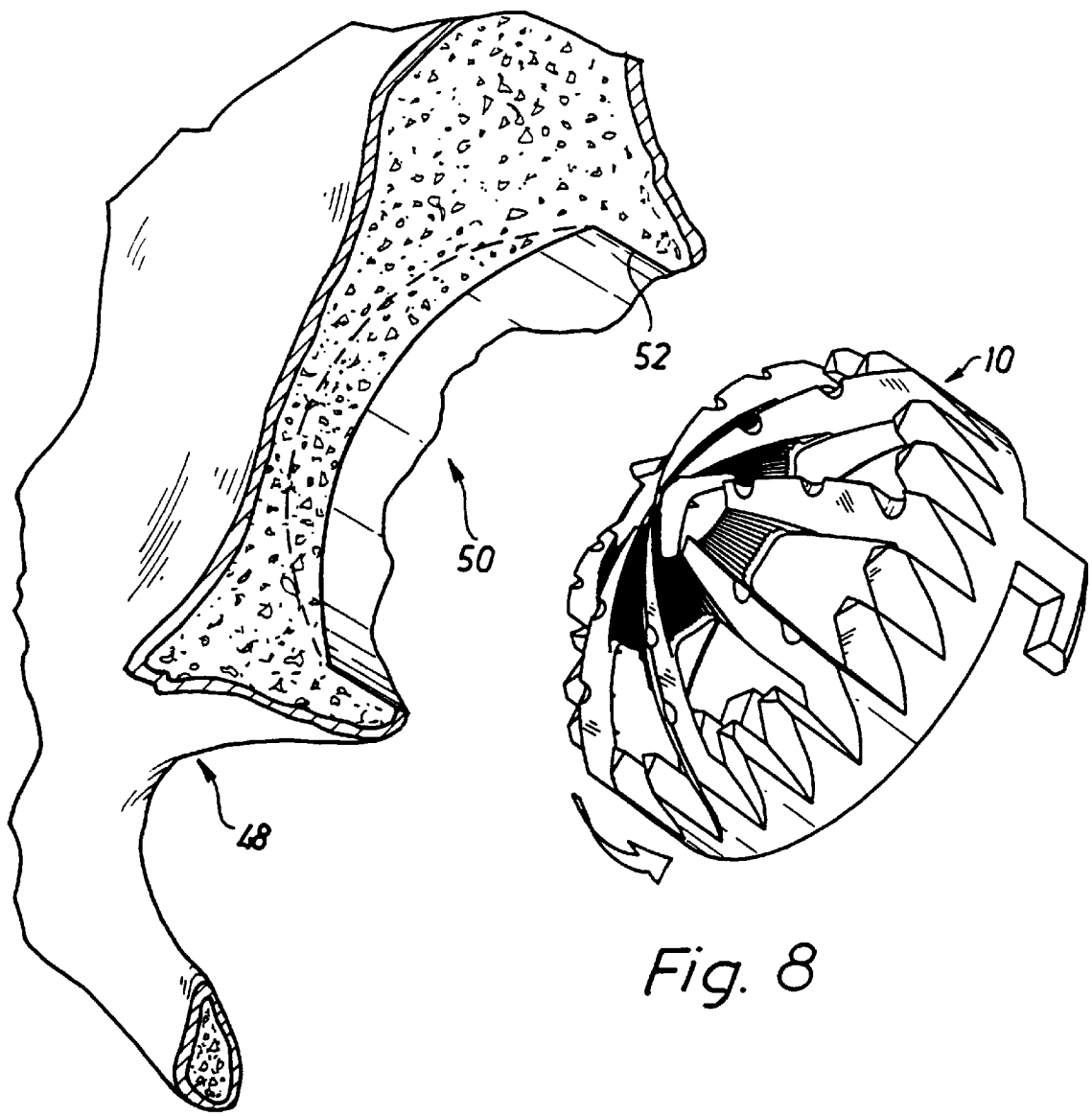
FIG. 8 is a schematic perspective view illustrating the use of the reamer in FIGS. 1–7 for shaping an acetabular cavity.

Referring now to FIGS. 1–7, wherein like parts are indicated by like reference numerals, there is illustrated a reamer or cutting head 10 in accordance with a preferred embodiment of the invention. This exemplary embodiment is especially intended for reaming acetabular cavities (acetabulae) in connection with the implantation of acetabular prosthesis cups. A method of using the cutting head 10 for this purpose is illustrated in FIG. 8.

With respect to the overall design, the cutting head 10 is divided into three integrated parts: a cage-like, dome-shaped top portion 12, a cylindrical base portion 14, and quick-release means in the form of two hooks 16 by which the cutting head 10 can be releasably connected to a handle member (not shown) for rotating the cutting head about a rotational axis A. Both the dome-shaped top portion 12 and the cylindrical base portion 14 have circular cross-sections concentric with the axis A.

Figure 1:
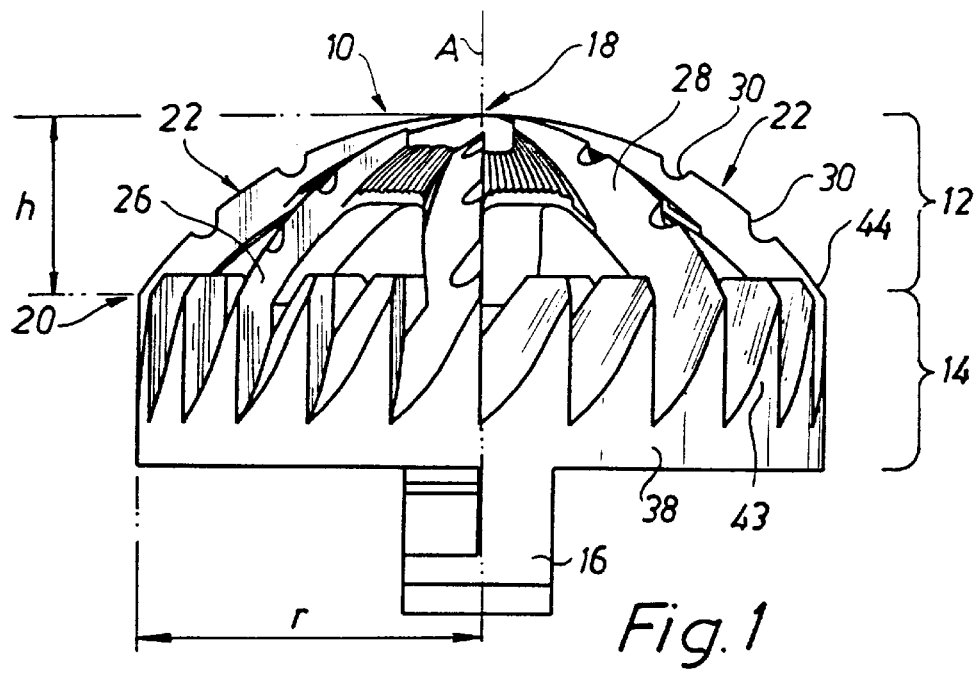
Figure 2:
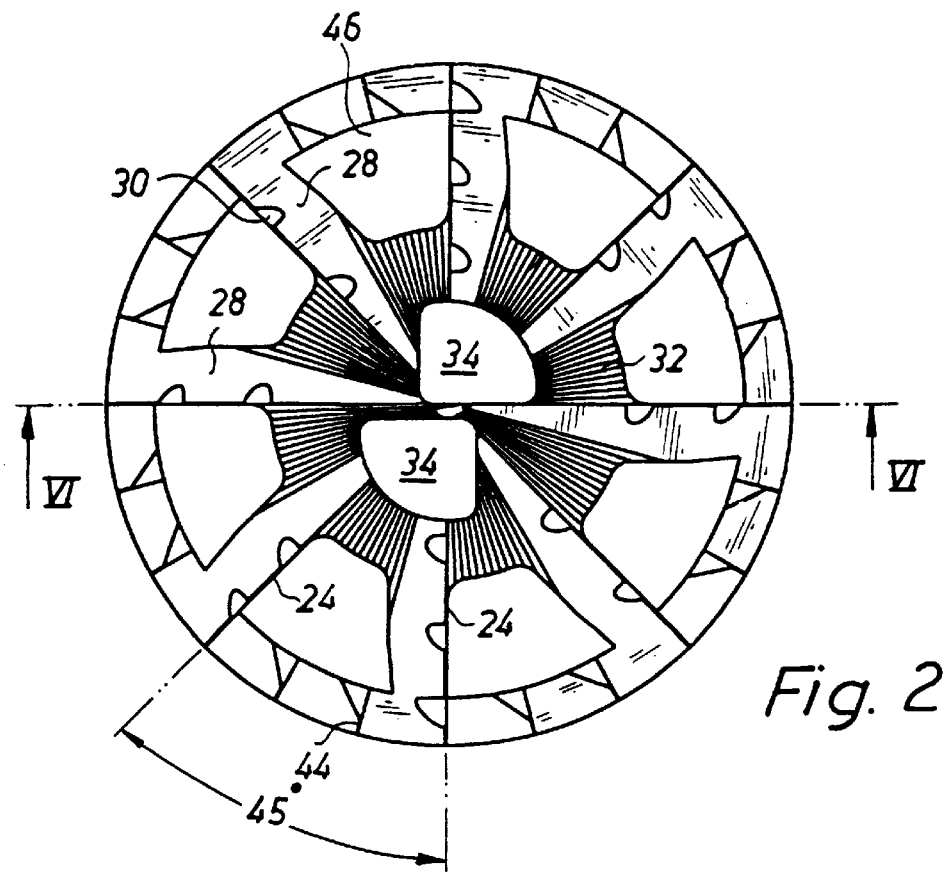
Figure 3:
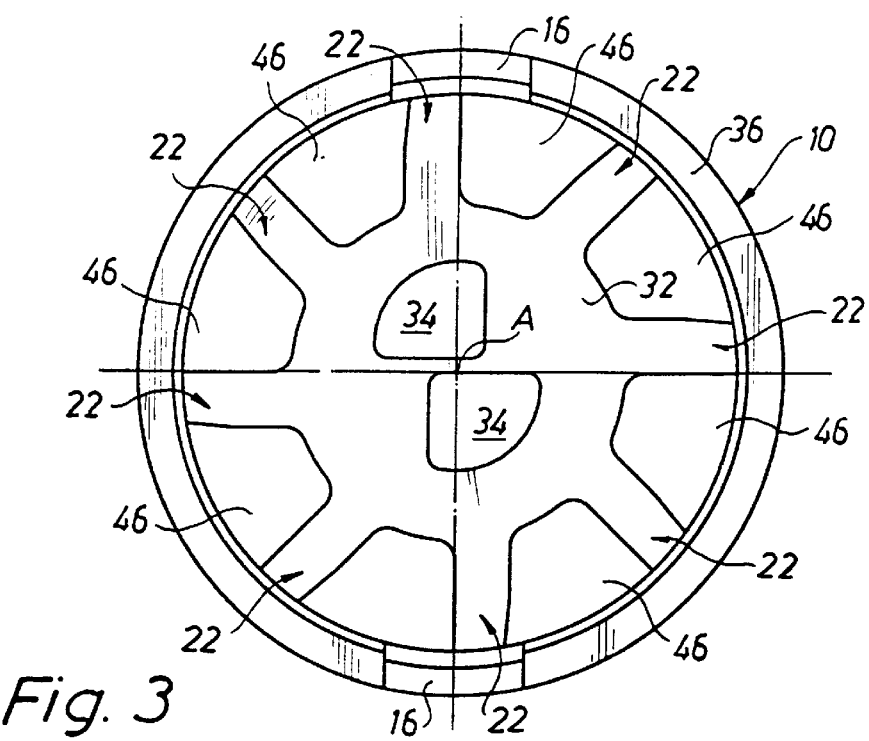
Figure 7:
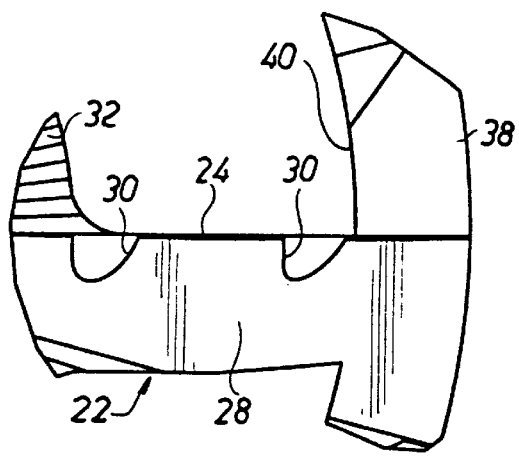
Figure 6:
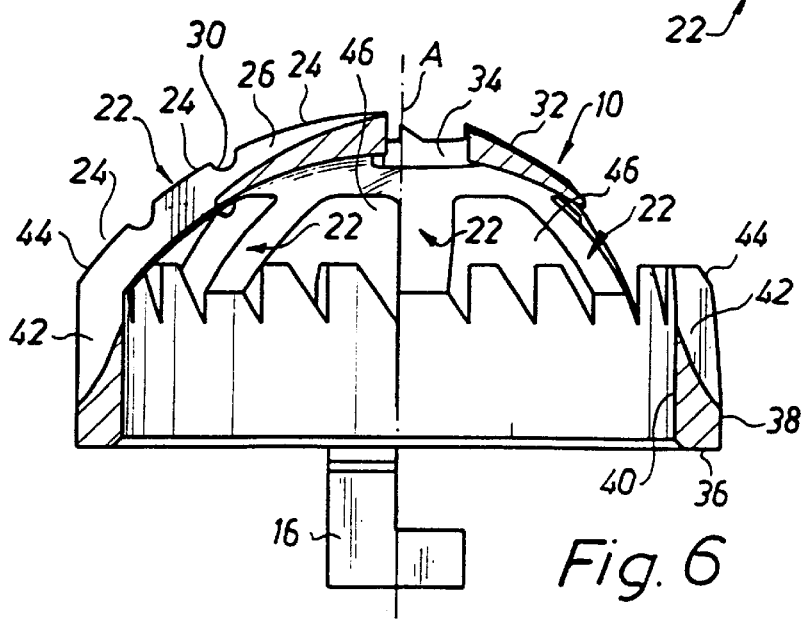
Figure 4:
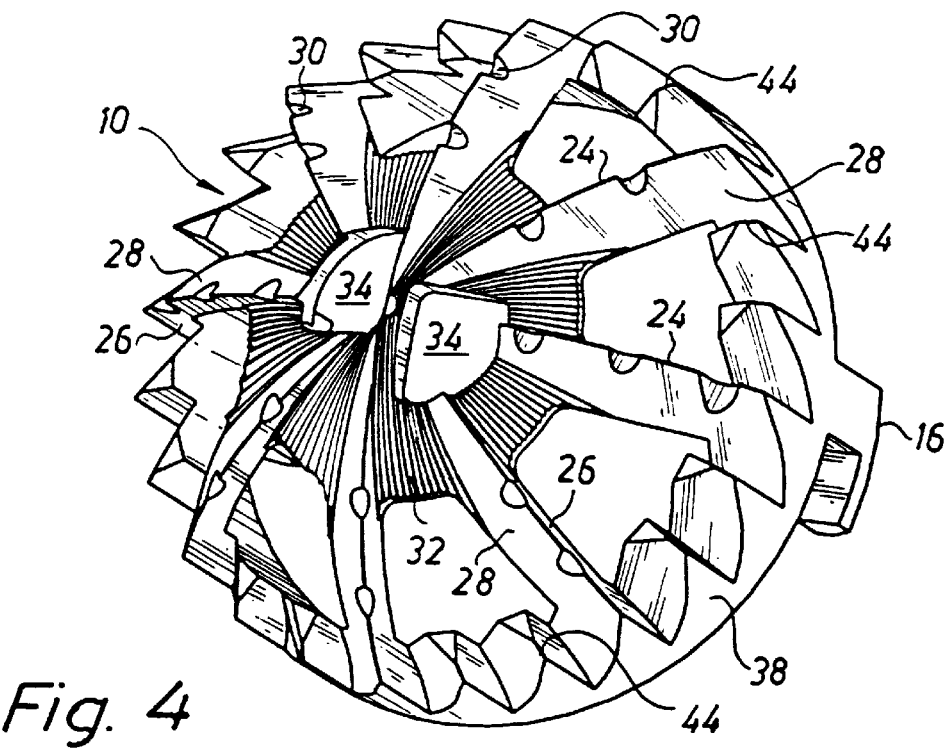
Figure 5:
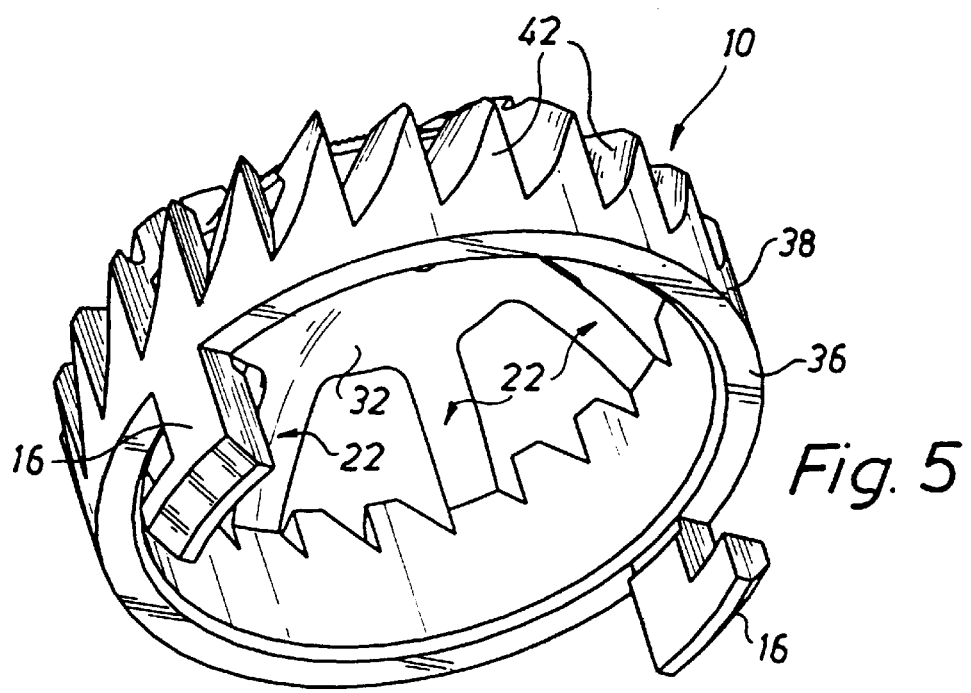

The dome-shaped top portion 12 has the form of a truncated hemispherical dome, i.e. a hemispherical dome truncated at its base portion. Thus, as indicated in FIG. 1, the height h is less than the radius r. The truncated dome presents a pole region 18 and a base region 20 interconnected by eight legs 22, which are arranged at angulary spaced intervals (45°) with respect to the axis A. The curvature of the legs 22 defines the curvature of the truncated dome. Each leg 22 forms a relatively long main cutting edge 24. In this embodiment, the cutting edge is formed by a cutting surface 26 laying in a radial plane parallel to the axis A, and a release surface 28 inclined relative to the cutting surface 26.

A plurality of notches 30 are formed in the main cutting edges 24, dividing each of the main cutting edges 24 into smaller cutting edges. In this embodiment, two or three notches 30 are formed in each leg 22. As seen in the top elevational view in FIG. 2, the notches 30 of two adjacent legs 22 are located at different radial positions. This results in that said smaller cutting edges will be arranged in a spiral fashion about the axis A, as will be evident from FIG. 2. This arrangement of the cutting edges 24 is referred to as ribbed cutting edges, and the purpose thereof has been indicated above.

At the pole region 18 of the truncated dome, the legs 22 are interconnected by means of a ring-shaped structure 32. Two of the legs 22 (the ones which are directed along the line VI—VI in FIG. 2) extend all the way to and beyond the axis A, in order to ensure that also the bottom of the acetabular cavity is reamed. The legs 22 and the ring-shaped structure 32 define two top openings 34 in the pole region 18 of the truncated dome.

The cylindrical base portion 14, which is integrated with the top portion 12, is in the form of a cylindrical ring having a smooth bottom surface 36, a smooth outer cylindrical surface 38, a smooth inner cylindrical surface 40 and a top which is provided with a number of sawtooth-like projections 42. Seen in a radial direction towards the axis A, each projection 42 has a triangular cross-section. The radially outer surface 43 of each projection 42 is contiguous with the cylindrical outer surface 38. An outer inclined portion of the apex of each projection 42 forms a relatively short peripheral cutting edge 44.

In the illustrated embodiment, twenty-four peripheral cutting edges 44 are distributed at angulary spaced intervals (15°) along the circumference of the base portion 14. Thus, there are three times as many peripheral cutting edges 44 than main cutting edges 24. One third of the peripheral cutting edges 44 are actually formed by the end portions of the main cutting edges 22. Thereby, the legs 22 are supported by and connected to the cylindrical base portion 14.

The combination of the legs 22, the ring-shaped structure 32 and the projections 42 defines eight relatively large through openings 46 in the dome-shaped top portion 12, communicating with an internal chamber in the cutting head 10. As apparent from the drawings, the cutting head 10 presents an essentially open, cage-like design.

The use of a reamer or cutting head 10 according to the embodiment disclosed in FIGS. 1–7 will now be described with reference to FIG. 8. FIG. 8 illustrates a part of a human pelvis 48 with a acetabular cavity (acetabulum) 50 prepared by a cutting head 10 shown in a retracted position. The outer contour of the cutting head 10, i.e. the truncated dome-shape and the cylindrical base portion, corresponds to the inner contour of the prepared cavity 50. Thus, the cavity 50 has been reamed to such an extent, that the dome-shaped portion, i.e. the cutting edges 24 and 44, has shaped a cylindrical inner wall portion 52 at the entrance opening of the cavity 50. During the reaming operation, this cylindrical inner wall portion 52 provides a guiding surface for the cylindrical outer surface 38 of the cutting head. Subsequently to the reaming operation, an acetabular cup, especially of the design disclosed in the above-mentioned WO 95/17140, may be inserted into the prepared cavity, such that a cylindrical base portion of the cup is received with a tight fit in the cylindrical entrance portion of the socket.

Several modifications of the embodiment described above are conceivable within the scope of the appended claims. For example, the number of legs 22 and the number of projections 42 may be varied. In fact, it might be possible to use only one single leg 22. Furthermore, the top portion 12 may have other shapes than the disclosed dome shape. Also, the cutting head 10 may be designed as a more compact structure without any internal hollow chamber, and in that case the cut-off debris has to be removed by channel means or the equivalent arranged between the main cutting edges. In a more simple embodiment, the notches 30 may be dispensed with. The peripheral cutting edges 44 may be completely separate from the main cutting edges 24. Finally, the main cutting edges 24 and/or the peripheral cutting edges 44 may be distributed at varying angular spacings in order to avoid interference phenomena.

What is claimed is:

1. A reamer for shaping a bone socket, comprising a cutting head having a top which in use is directed towards the bone socket, and a base axially spaced from the top along a rotational axis of the cutting head, said cutting head being provided with cutting means for removing material from the socket during rotation of the cutting head about the rotational axis, wherein said cutting means comprises:

a number of relatively long main cutting edges, each of which extends in a direction from the base to the top, and a number, higher than said number of main cutting edges, of relatively short peripheral cutting edges, which are located at the base of the cutting head and distributed at angulary spaced intervals about said rotational axis.

2. The reamer as claimed in claim 1, wherein the number of said peripheral cutting edges is at least twice the number of said main cutting edges.

3. The reamer as claimed in claim 1 or 2, wherein the cutting head comprises a portion in the shape of a dome having a base region and a pole region wherein the pole region defines said top of the cutting head.

4. The reamer as claimed in claim 3, wherein said dome-shaped portion of the cutting head has the form of a hemispherical dome.

5. The reamer as claimed in claim 3, wherein said dome-shaped portion of the cutting head has the form of a hemispherical dome, which is truncated at its base region.

6. The reamer as claimed in claim 3, wherein each of said main cutting edges extends from the base region of the dome to the pole region of the dome.

7. The reamer as claimed in claim 3, wherein at least one of said main cutting edges extends all the way up to a point where the axis intersects with the dome.

8. The reamer as claimed in claim 1, wherein each of said main cutting edges lies in a respective radial plane relative to the rotational axis.

9. The reamer as claimed in claim 1, wherein some of the peripheral cutting edges are formed by end portions of the main cutting edges, whereas the rest of the peripheral cutting edges are formed as individual cutting edges separate from the main cutting edges.

10. The reamer as claimed in claim 1, wherein each of said main cutting edges is formed by a respective leg, extending between and interconnecting the top and the base of the cutting head, and wherein material-receiving openings are provided between the legs for guiding cut-off material into an interior chamber of the cutting head.

11. The reamer as claimed in claim 1, wherein the base of the cutting head has a cylindrical outer peripheral surface concentric with and parallel to the rotational axis, whereby, in use of the reamer, said cylindrical outer peripheral surface is received at least partly in the socket and guided thereby for preventing unintentional tilting of the rotational axis.

12. The reamer as claimed in claim 11, wherein the cylindrical outer peripheral surface of the cutting head is designed not to have any cutting effect, but only to accomplish said tilt-preventing guiding effect.

13. The reamer as claimed in claim 1, wherein said number of main cutting edges is at least two.

14. The reamer as claimed in claim 13, wherein the main cutting edges are symmetrically distributed about the rotational axis.

15. The reamer as claimed in claim 13, wherein the main cutting edges are asymmetrically distributed about the rotational axis.

16. The reamer as claimed in claim 13, wherein the main cutting edges are ribbed.

17. A kit for use in orthopedic surgery, comprising in combination a reamer as claimed in claim 1 for the preparation of a bone socket, and a cup-shaped prosthesis component for implantation in said bone socket.

18. A method for implanting a prosthesis component in a bone socket, the prosthesis component presenting a dome-shaped portion and a cylindrical base portion, the method comprising the following steps:

shaping said bone socket to a desired form for receiving the prosthesis component, wherein said shaping is performed by the use of a rotational-type reamer having a cutting head, which comprises a top portion provided with cutting means for the removal of material from said bone socket, wherein, during said shaping, the top portion of the cutting head is completely received in the bone socket to such an extent, that a cylindrical entrance portion is formed in the socket by said cutting means, and inserting the prosthesis component into said bone socket wherein the cylindrical base portion of the prosthesis is received with a tight fit in the cylindrical entrance portion of the socket in order to restrict tilting of the thus inserted prosthesis component.

19. The method as claimed in claim 18, wherein the cutting head is further provided with a cylindrical base portion, which, during said step of shaping the bone socket, is received at least partly in said cylindrical entrance portion of the socket.

* * * * *